United States Patent [19]

Holzknecht et al.

[11] Patent Number: 4,795,571
[45] Date of Patent: Jan. 3, 1989

[54] PURIFICATION OF FROZEN CRYSTAL LAYERS

[75] Inventors: Bernhard Holzknecht, Ellerstadt; Hugo Fuchs, Ludwigshafen; Eckhard Hetzel, Bobenheim-Roxheim; Klaus Wintermantel, Weinheim; Peter Thoma, Frankenthal, all of Fed. Rep. of Germany

[73] Assignee: Basf Aktiengesellschaft, Ludwigshafen, Fed. Rep. of Germany

[21] Appl. No.: 154,227

[22] Filed: Feb. 10, 1988

[30] Foreign Application Priority Data

Feb. 20, 1987 [DE] Fed. Rep. of Germany ....... 3705388

[51] Int. Cl.$^4$ .............................................. B01D 9/04
[52] U.S. Cl. ..................... 210/774; 62/532
[58] Field of Search ................ 210/774, 175, 177–179, 210/181, 182, 187; 62/532, 537, 540, 541, 542, 544

[56] References Cited

FOREIGN PATENT DOCUMENTS 1769123 2/1976 Fed. Rep. of Germany .
2606364 7/1981 Fed. Rep. of Germany .
1083850 9/1967 United Kingdom .

Primary Examiner—Frank Sever
Attorney, Agent, or Firm—Keil & Weinkauf

[57] ABSTRACT

Frozen crystal layers are purified by a process in which these crystal layers, after they have been frozen out from a melt or solution on a cooling surface, are brought into contact with a purifying liquid and thus purified over their entire thickness, after which the said layers are separated from the purifying liquid and then melted, wherein the temperature of the crystal layers and of the purifying liquid is close to the melting point or solubility temperature, mass transfer at the phase boundary is intensified by forced convection, and this purification is carried out in the course of from 1 to 60 minutes on layers having a thickness of from 0.2 to 10 mm.

8 Claims, 1 Drawing Sheet

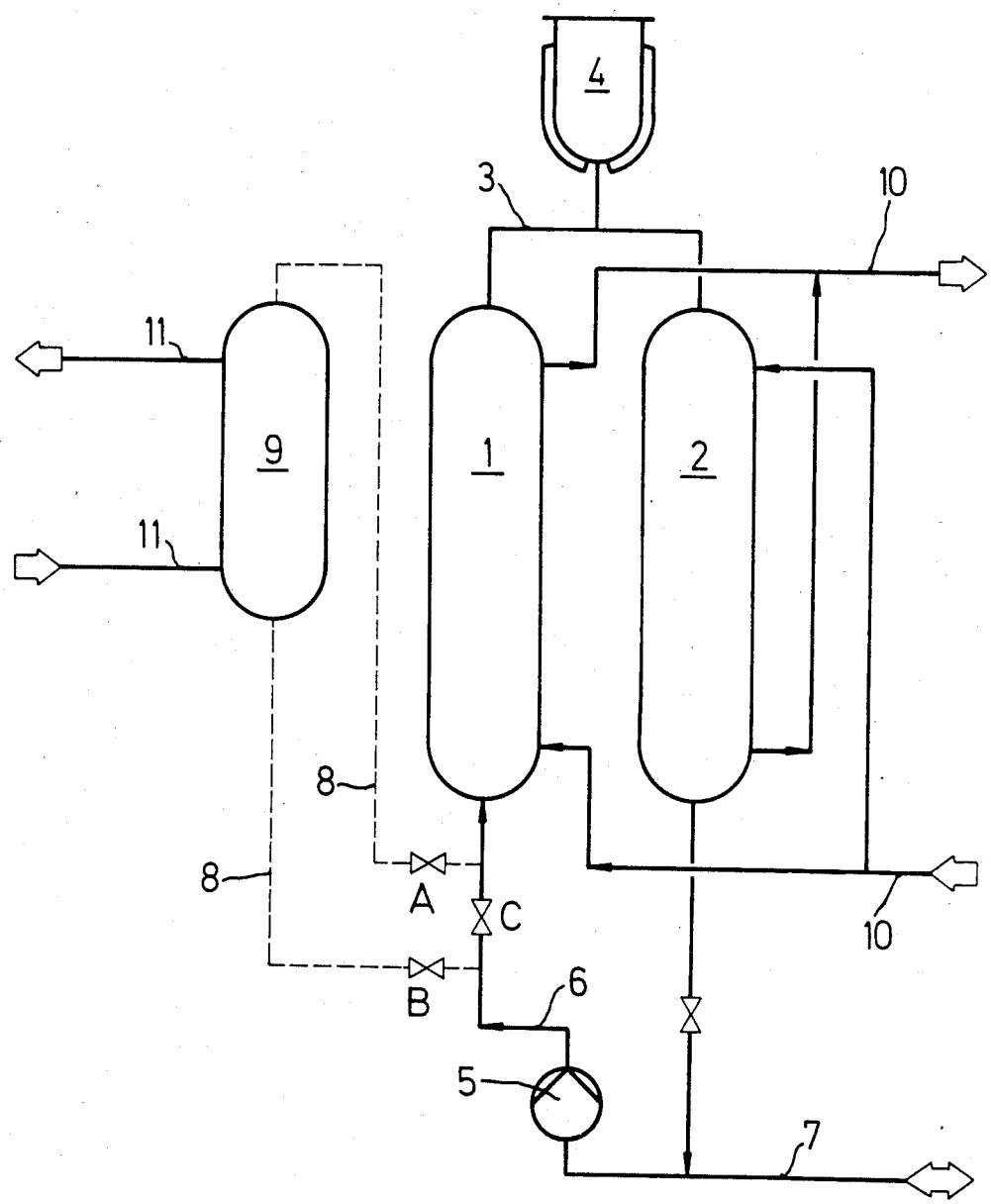

PURIFICATION OF FROZEN CRYSTAL LAYERS

The present invention relates to a process for the purification of frozen crystal layers, in which the latter, after they have been frozen out from a melt or solution on a cooling surface, are brought into contact with a purifying liquid and thus purified over their entire thickness, after which the said layers are separated off from the purifying liquid and then melted.

British Patent No. 1,083,850 discloses a process for fractional crystallization, in which a melt is passed several times through a pipe, the pipe is cooled, the residual liquid is removed and the crystals are then melted. During this procedure, the melt is continuously supplied with heat in order to obtain a smooth crystal surface. German Laid-Open Application No. DOS 2,606,364 describes an improved process for the fractional crystallization of liquid mixtures, in which the said mixture is passed repeatedly in turbulent flow through an indirectly cooled crystallization zone, for example a pipe, with the proviso that the crystallization zone is always full, the residual liquid is removed after deposition of the crystal layer on the wall of the crystallization zone, the surface of the crystal layer is washed with a mixture which corresponds to the initial composition, and the crystal layer is then melted. In this procedure, washing of the crystal layer comprises displacement of the film of residual liquid adhering to the crystal surface by a liquid film of starting material. Furthermore, German Laid-Open Application No. DOS 1,769,123 describes a process in which the melt to be crystallized is passed as a falling film through indirectly cooled crystallization zones, and the crystal layer deposited is separated from the residual liquid and then melted. In all three of the processes described, freezing has to be carried out repeatedly in one or more successive stages in order to achieve higher purity than that obtained by crystallizing out once. This requires a correspondingly larger apparatus and greater energy.

It is an object of the present invention to overcome the abovementioned disadvantages of the known processes.

We have found that this object is achieved, according to the invention, by a process for purifying frozen crystal layers without repeated crystallization, in which the crystal layers, after they have been frozen out from a melt or solution, are brought into contact with a purifying liquid for from 1 to 60 minutes and thus purified over their entire thickness, the layers and the liquid being thermostated at a temperature close to the melting point or the solubility temperature and forced convection taking place at the phase boundary, after which the said layers are separated from the purifying liquid and then melted. This purification process requires no additional energy for heating or cooling since the temperature of the cooling surface must in any case be increased above the melting point between freezing and melting. Moreover, the necessary residence time in the apparatus is substantially shorter than for freezing, so that the size of the apparatus is likewise substantially smaller than for a further crystallization stage. For a required purity of the end product, relevant purification of the frozen layers results in fewer crystallization stages being required than without purification of the layers. Consequently, both the crystallizers and the number of receivers required for each stage, and the energy requirement, are smaller than without purification.

The purification process is applicable to layers which have been frozen out of melts or solutions. Fractional crystallization from the melt has become particularly important industrially. Suitable substances are organic compounds which have a melting point of from $-50$ to $+200°$ C. and do not decompose at the temperatures used. Examples of suitable substances are caprolactam, toluylene diisocyanate, piperazine and naphthalene.

The crystal layers subjected to purification can remain fixed to the cooling surface on which they have grown or can be scraped off. In the former case, the purifying liquid is allowed to flow over the layer; in the second case, the crystal layer is wet on both sides and is suspended in fragments, for example as flakes, in the purifying liquid, or the said liquid flows past the said layer in a fixed bed. The purifying liquid used is the melt or solution of the product. This contact produces a purification effect whereby components to be removed are transferred from the layer to the purifying liquid.

An essential feature of the invention is that the temperature of the layer during purification is close to the melting point or solubility temperature. This promotes and accelerates transfer of the impurities. If the crystal layers are suspended in the purifying liquid, a further result is that the solids content remains constant. If the crystal layers are still present on the cooling surface, the temperature of the latter, which is substantially below the melting point/solubility temperature during freezing out, is increased to this value. The purification effect is reinforced if the temperature of the cooling surface is increased to up to 5K above the equilibrium temperature. This may result in partial melting of the crystal layers. To avoid loss of crystals, the temperature is then steadily decreased again to slightly below the equilibrium temperature until the solids content has reattained its value.

Another essential feature of the invention is intensive mass transfer at the phase boundary. If the crystal layers are still present on the cooling surfaces, the purifying liquid is repeatedly circulated through the crystallization zones. The crystalization zones may be in the form of pipes, square channels or other closed sections or in the form of sheets. The required intensive mass transfer is achieved in this case by an appropriate flow rate which is generated in the pipe flow, in a falling film or in flow over a sheet. It is in a range from 0.2 to 6 m/s. In the other case where detached crystal layers are suspended in the purifying liquid, the required mass transfer is produced by suitable measures, for example stirring or circulation.

Another essential feature of the invention is the time during which the crystal layer is in contact with the purifying liquid. The rate of mass transfer decreases steadily from an initial maximum value. Purification can be terminated when this rate falls below a limiting value. The purification times are from 1 to 60 minutes and also depend on a further feature of the invention, the layer thickhess. The layer thickness and purification time must be matched with one another. The thickness of frozen layers is from 0.2 to 10 mm.

A further essential feature of the invention is the initial concentration, in the purifying liquid, of those components which are to be removed from the crystal layer. A fairly low concentration of impurities in the purifying liquid also leads to fairly low concentrations of impurities in the crystal layer. However, a purification effect is also obtained if the concentration of impurities in the purifying liquid is higher than that in the crystal layer. In particular, the concentration of impurities in the residual liquid (mother liquor) is substantially higher than that in the crystals after the freezing procedure, this being due to the associated separation effect. If this mother liquor is subsequently used as the purifying liquid, ie. the crystal layer remains in contact with the same liquid, a purifying effect likewise occurs.

Thus, the mother liquor from the freezing process or a part stream of the molten/dissolved purified crystals, or both in succession in the order of increasing purity, can be used as the purifying liquid. In the case of detached and suspended crystal layers, this procedure can also be carried out continuously. In this case, the crystal layers are fed in countercurrent to the purifying liquid.

The drawing shows the best mode of the invention.

The two Examples which follow (purification of caprolactam and separation of toluylene iiisocyanate isomers) illustrate the procedure in the purification process.

EXAMPLE 1

Layer Crystallization and Purification of Caprolactam

Starting material: dehydrated crude lactam, temperature=76° C.

Melting point about 69° C.

UV 2,579.

PTN 950.

The purity of caprolactam is usually indicated by the UV number (UV) and the permanganate titration number (PTN). The permanganate titration number shows the consumption of 0.1 normal potassium permanganate solution in ml, based on 1 kg of caprolactam in strongly acidic solution. The UV number is defined as follows:

Principle: The absorption of the caprolactam is measured in the spectral range from 360 to 270 nm, and after conversion, is expressed as a characteristic number.

Analytical apparatus: 1 recording single-beam spectrophotometer (Carl Zeiss DMR/21), 1 200 ml conical flask, 2 10 cm long quartz cells with covers (path length 10 cm).

Method: 50 g of caprolactam are dissolved in 50 g of cold doubly distilled water in a conical flask. This solution is introduced into a cell up to the calibration mark. The second cell is filled with the same doubly distilled water, which constitutes the reference solution.

Both cells are now closed with the covers, the ground surfaces are cleaned with tissue paper and the cells are inserted into the cell holders. The spectrum is then recorded between 370 nm and 260 nm as described in the instructions for the apparatus. The recording speed is 50. The extinction measurement is carried out on the scale 0-1.

When recording is complete, a mark is made on the paper every 10 nm from 270 to 360 nm.

Evaluation: From the graph, extinctions are read off at 270, 280, 290, 300, 310, 320, 330, 340, 350 and 360 nm and are summed.

The sum of the 10 extinction values is multiplied by 2 to give the UV characteristic number. The UV characteristic number is thus always based on 100% strength caprolactam and on a path length of 10 cm.

Procedure

1. Filling

The crystallizers 1, 2 are brought to 60° C. by the secondary circulation 10. A thin layer of seed crystals is present on the cooling surfaces from the previous crystallization cycle (produced by a crystallized falling film after removal of the melt). The starting material is pumped by pump 5 via connection 7 into the crystallizers 1, 2. The valves A and B are closed while valve C is open. The filling process is complete when the level measurement in equilibration vessel 4 responds. During the filling process, which takes about 1 minute, the temperature of the secondary circulation is increased from 60° C. to 64° C. The amount introduced is 12.34 kg of starting material.

2. Crystallization

When filling is complete, the melt is circulated through crystallizer 1, connection 3, crystallizer 2 and pump 5. During this procedure, the temperature of the secondary circulation is increased from 64° C. to 66° C. in 3 minutes and then reduced from 66° C. to 51° C. in 75 minutes. The volume stream circulated is initially 1.47 m³/h. As a result of crystallization of the crystal layer on the inside of the pipe and partial blocking of the flow crosssection, the volume stream circulated decreases. The crystallization process is complete when the volume stream has reached a limiting value of 0.30 m³/h. The time for the crystallization process is 78 minutes.

3. Purification with the mother liquor

The temperature of the secondary circulation is increased to 72° C. The volume flow increases slightly (0.45 m³/h). After a short residence time, the temperature is reduced again to about 51° C. until the volume flow has again reached the final value of 0.30 m³/h after the crystallization process. The duration of this step is 10 minutes.

The mother liquor is then discharged via connection 7.

Amount: 7.31 kg.

Mother liquor: UV 3,958.

PTN 1,500.

4. Purification with pure lactam

Pure lactam prior to purification: UV 870.

PTN 385.

The temperature of the secondary circulation is increased to 71° C. 6.99 kg of pure lactam are introduced via connection 7 and pump 5 for purification purposes and are then circulated for 20 minutes. The volume flow increasss to 0.45 m³m/h. Toward the end of the purification step, the temperature of the secondary circulation is again reduced to about 48° C., so that the volume flow again reaches 0.30 m³m/h. The pure lactam is then discharged via connection 7. Amount: 7.02 kg.

Pure lactam after purification: UV 925.

PTN 385.

5. Melting and discharging

The crystals are now melted by increasing the temperature of the secondary circulation to above the melting point. This is done so that sampling can be carried out without mixing. Otherwise, molten crystals are introduced and circulated, and the heat of fusion is supplied via heat exchanger 9. After melting, the crystals are discharged via connection 7. The amount of crystals is 5 kg.

Crystals: UV 499.

PTN 230.

The secondary circulation is very rapidly brought to 50° C. (about 20 K below the melting point) directly after the crystals have been discharged, in order that the falling film adhering to the cooling surfaces crystallizes through as a layer of seed crystals for the next cycle.

In comparison, the values for crystals without purification are: UV 1033.
PTN 375.

EXAMPLE 2

Layer Crystallization and Purification of Toluylene Diisocyanate (TDI) Isomers for Isomer Resolution Starting material: 80.24% of 2,4-TDI.
19.76% of 2,6-TDI.
Temperature: 21.4° C.

Procedure:

1. Filling

The crystallizers 1, 2 are brought to 6° C. by means of secondary circulation 10. A thin layer of seed crystals is present on the cooling surfaces from the previous crystallization cycle (produced by crystallized falling film after removal of the melt). The starting material is pumped by pump 5 via connection 7 into the crystallizers 1, 2. The valves A and B are closed and valve C is open. The filling process is complete when the level measurement in equilibration vessel 4 responds. During the filling process, which takes about 1 minute, the temperature of the secondary circulation is increased from 6° C. to 7° C.

Amount introduced: 16 kg.

2. Crystallization

When filling is complete, the melt is circulated through crystallizer 1, connection 3, crystallizer 2 and pump 5. During this procedure, the temperature of the secondary circulation is increased from 7° C. to 10° C. in 3 minutes and from 10° C. to 13° C. in 6 minutes, kept at 13° C. for 40 minutes, reduced to 9° C. in the course of 4 hours and then reduced to 3° C. in the course of a further 71 minutes. The volume flow circulated is initially 1.67 m³/h. As a result of crystallization of the crystal layer on the inside of the pipe and partial blocking of the flow cross-section, the volume flow circulated decreases. The crystallization process is complete when the volume flow has reached a limiting value of 0.41 m³/h. The time for crystallization is 360 minutes.

The mother liquor is then discharged via connection 7. Amount: 11 kg.

Mother liquor: 74.79% of 2,4-TDI.
25.21% of 2,6-TDI.

3. Purification with 2,4-TDI

Purifying liquid before purification: 99.32% of 2,4-TDI. 0.68% of 2,6-TDI.

The temperature of the secondary circulation is increased to 19° C. 11 kg of purifying liquid is introduced via connection 7 and pump 5 and is then circulated for 45 minutes. The volume flow is 0.78 m³/h. Toward the end of the purification step, the temperature of the secondary circulation is again reduced to about 15° C., so that the volume flow reaches 0.74 m³/h. The 2,4-TDI is then discharged via connection 7. Amount: 11 kg.

Purifying liquid after purification: 96.99 of 2,4-TDI. 3.01% of 2,6-TDI.

5. Melting and discharge

The crystals are then melted by increasing the temperature of the secondary circulation to above the melting point; this is done so that sampling can be carried out without mixing. Otherwise, molten crystals are introduced and circulated, and the heat of fusion is supplied via heat exchanger 9. After melting, the crystals are discharged via connection 7. Amount: 5 kg.

Crystals: 98.33% of 2,4-TDI. 1.67% of 2,6-TDI.

The secondary circulation is very rapidly brought to 0° C. (about 20K below the melting point) directly after the crystals have been discharged, in order that the falling film adhering to the cooling surfaces crystallize through as a layer of seed crystals for the next cycle.

From other experiments *without* purification with 2,4-TDI, the following result is obtained for the crystals: 92.55% of 2,4-TDI. 7.45% of 2,6-TDI.

We claim:

1. A process comprising: purifying frozen crystal layers after they have been frozen out from a melt or solution on a cooling surface, in a single crystallization by contacting with a purifying liquid and thus purifying over their entire thickness, thereafter separating said layers at a flow rate of 0.2 to 6 M/s from the purifying liquid and then melting, while providing matched process variables including a temperature of the crystal layers and of the purifying liquid is close to the melting point or solubility temperature, and a crystallization time of from 1 to 60 minutes on layer thicknesses of from 0.2 to 10 mm.

2. A process as claimed in claim 1, wherein mass transfer at the phase boundary is intensified by forced convection.

3. A process as claimed in claim 1, wherein the cooling surface is a flat or cylindrical surface.

4. A process as claimed in claim 1, wherein the crystal layers adhere to the cooling surface during purification and are wet on one side by the purifying liquid, or they are detached from the cooling surface and are wet on both sides by the purifying liquid.

5. A process as claimed in claim 1, wherein the concentration, in the purifying liquid, of components to be removed are less than or greater than that in the crystal layer.

6. A process as claimed in claim 1, wherein the purifying liquid used is the residual liquid from a preceding crystallization, or a fresh melt or solution brought into contact with the crystal layer, said fresh melt or solution being molten or dissolved purified crystals.

7. A process as claimed in claim 1, wherein a purifying liquid is used alone or a plurality of purifying liquids are used in succession in order of increasing purity, or crystal layers and purifying liquid are fed continuously in countercurrent with respect to one another.

8. A process as claimed in claim 1, wherein the temperature of the crystal layer is initially steadily increased to up to 5K above the equilibrium temperature during the purification process, and is steadily reduced again at the end to slightly below the equilibrium temperature.

* * * * *